United States Patent [19]

Jackson

[11] Patent Number: 5,786,501
[45] Date of Patent: Jul. 28, 1998

[54] PROCESS FOR THE PREPARATION OF PURE ALKYL ALKYLACETOACETATES

[75] Inventor: Barry Jackson, Brig-Glis, Switzerland

[73] Assignee: Lonza AG, Gampel/Valais, Switzerland

[21] Appl. No.: 806,051

[22] Filed: Feb. 25, 1997

[30] Foreign Application Priority Data

Mar. 13, 1996 [CH] Switzerland .................. 0655/96
Apr. 30, 1996 [CH] Switzerland .................. 1087/96

[51] Int. Cl.$^6$ .................. C07C 69/72; C07C 69/66
[52] U.S. Cl. .................. 560/178; 560/174
[58] Field of Search .................. 560/178, 174

[56] References Cited

U.S. PATENT DOCUMENTS

| | | | |
|---|---|---|---|
| 2,843,623 | 7/1958 | Hansley et al. | 560/178 |
| 2,900,311 | 8/1959 | Montagna et al. | 560/178 |
| 3,839,418 | 10/1974 | Hinton et al. | 260/483 |
| 4,684,743 | 8/1987 | Gramlich et al. | 558/374 |
| 4,806,670 | 2/1989 | Gramlich et al. | 558/371 |

FOREIGN PATENT DOCUMENTS

| | | |
|---|---|---|
| 100019 | 2/1984 | European Pat. Off. |
| 2060443 | 12/1970 | Germany |

OTHER PUBLICATIONS

Helv. Chim. Acta, vol. 70, (1987), 196–197.
Organikum, 15, (1976), pp. 571 and 632.
W. Hunter, "German Acetylene Chemical Industry Ethyl–Aceto–Acetate", pp. 1–26, Dec. 1946.

*Primary Examiner*—Gary Geist
*Assistant Examiner*—Rosalynd A. Keys
*Attorney, Agent, or Firm*—Fisher, Christen & Sabol

[57] ABSTRACT

A process for the purification of alkyl alkylacetoacetates of the general formula:

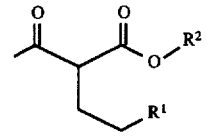

in which $R^1$ is a $C_1$–$C_{10}$-alkyl group and $R^2$ is a $C_1$–$C_4$-alkyl group. In the process, an alkyl alkylacetoacetate which contains an alkyl alkenylacetoacetate of the general formula:

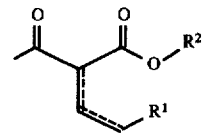

in which $R^1$ and $R^2$ have the above-stated meaning, and/or further by-products as an impurity, is converted with an ester of the general formula:

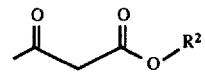

in which $R^2$ has the above-stated meaning, in the presence of a base, into an intermediate which is separated off.

6 Claims, No Drawings

PROCESS FOR THE PREPARATION OF PURE ALKYL ALKYLACETOACETATES

BACKGROUND OF THE INVENTION

1. Field Of The Invention

The invention relates to a process for the preparation of pure alkyl alkylacetoacetates of the general formula:

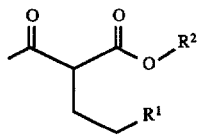

in which $R^1$ is a $C_1$–$C_{10}$-alkyl group and $R^2$ is a $C_1$–$C_4$-alkyl group, from alkyl alkylacetoacetates which, as an impurity, contain alkyl alkenylacetoacetates of the general formula:

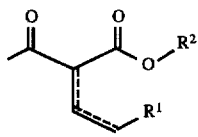

in which $R^1$ and $R^2$ have the above-stated meaning, and/or further by-products.

2. Background Art

Alkyl alkylacetoacetates are important intermediates for the production of pharmaceuticals. For example, methyl hexylacetoacetate is an important intermediate for the production of tetrahydrolipstatin [Helv. Chim. Acta, Vol. 70, (1987), 196–200]. For example, the preparation of methyl hexylacetoacetate starting from hexanal and methyl acetoacetate is known. In this process, hexanal and methyl acetoacetate are reacted, for example, by the classical Knoevenagel reaction [cf., for example, Organikum, (1976), p. 571] to give methyl hexenylacetoacetate, which is then hydrogenated in the presence of hydrogen to give the final product (German Published Patent Application No. 2,060,443). Such a process, however, has the disadvantage that the methyl hexylacetoacetate is contaminated by methyl hexenylacetoacetate which is difficult to remove.

BROAD DESCRIPTION OF THE INVENTION

The main object of the invention is to provide a simple purification process for alkyl alkylacetoacetates which achieves high purity product. Other objects and advantages of the invention are set out herein or are obvious herefrom to one skilled in the art.

The objects and advantages of the invention are achieved by the purification process of the invention.

The invention involves a process for the preparation of pure alkyl alkylacetoacetates of the general formula:

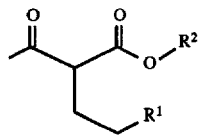

in which $R^1$ is a $C_1$–$C_{10}$-alkyl group and $R^2$ is a $C_1$–$C_4$-alkyl group, from alkyl alkylacetoacetates which contain alkyl alkenylacetoacetates of the general formula:

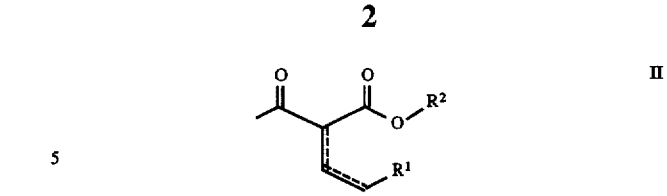

in which $R^1$ and $R^2$ have the above-stated meaning, and/or further by-products. The alkenylacetoacetic acid ester of the formula II is converted with an ester of the general formula:

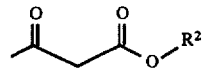

in which $R^2$ has the above-stated meaning, in the presence of a strong base, into an intermediate which is separated off.

DETAILED DESCRIPTION OF THE INVENTION

According to the invention, the alkyl alkylacetoacetate of the general formula:

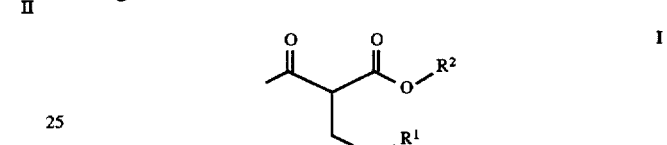

in which $R^1$ and $R^2$ have the above-stated meaning, which is contaminated with an alkyl alkenylacetoacetate of the general formula:

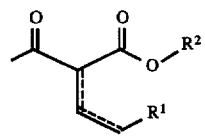

in which $R^1$ and $R^2$ have the above-stated meanings, and/or with further by-products, is purified in such a way that the alkyl alkenylacetoacetate of the general formula II is converted with an ester of the general formula:

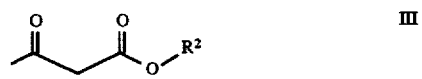

in which $R^2$ has the above-stated meaning, in the presence of a strong base, into an intermediate which is separated off.

The conversion of the alkyl alkenylacetoacetate into the intermediate can be carried out by the Michael reaction, which is well known by the art (cf., for example, Organikum, 1976, p. 632). The intermediate obtained is expediently a compound of the general formula:

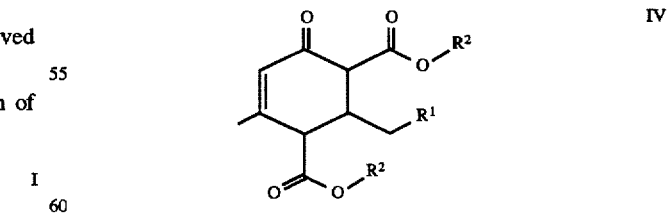

The radical $R^1$ is a $C_1$–$C_{10}$-alkyl, such as, methyl, ethyl, propyl, i-propyl, butyl, t-butyl, i-butyl, pentyl, hexyl, heptyl, octyl, nonyl or decyl. Preferably, $R^1$ is butyl or hexyl. The radical $R^2$ is a $C_1$–$C_4$-alkyl, such as, methyl, ethyl, propyl, i-propyl, butyl, t-butyl or i-butyl, and, preferably is methyl.

The esters of the general formula III, such as, methyl acetoacetate, are commercially available compounds.

As the strong base, alkali metal alkoxides can be used. As the alkali metal alkoxide, sodium or potassium methoxide, ethoxide, propoxide or butoxide can be used. Expediently, the alkali metal alkoxide corresponding to the ester is used. Preferably the strong base has a $pK_a$ of greater than 8. Expediently, the strong base is employed in the same molar amounts as the impurity present in the product (alkyl alkenylacetoacetate).

Expediently, the reaction of the alkyl alkenylacetoacetate of formula II with the ester of the general formula III is carried out at a temperature of from 50° to 150° C. and preferably at a temperature of from 80° to 110° C.

After a customary reaction time of 1 to 5 hours, the compound of the general formula IV or its decarboxylated derivatives is/are obtained.

The intermediate compounds of the general formula IV are then expediently removed by distillation. The distillation is preferably carried out under reduced pressure.

By this procedure, pure alkyl alkylacetoacetates are obtained which are contaminated with less than 0.4 percent of alkyl alkenylacetoacetate.

EXAMPLE 1

Preparation of methyl 2-hexylacetoacetate

The reaction mixture from the condensation of methyl acetoacetate (193.5 g) and hexanal (151.8 g) with piperidine catalysis was hydrogenated in an autoclave at 50° C. with hydrogen and Pd/C catalysis. After the end of the hydrogenation and filtering off the Pd/C catalyst, the two-phase mixture was concentrated at a pressure of 15 mbar and a temperature of 70° C. The residue (262 g) still contained 1.2 percent of methyl 2-hexenylacetoacetate. Methyl acetoacetate (3.14 g) and sodium methoxide (1.46 g of a 5.4 molar solution) were then added and this mixture was heated at 90° C. for 5 hours. At the end of this treatment, 0.39 percent of methyl 2-hexenylacetoacetate was still measured. The crude product was then distilled in a high vacuum (3 to 4 mbar) in a thin-layer evaporator. The methyl 2-hexylacetoacetate distillate (240.9 g), with a content of 97.8 percent, still contained 0.26 percent of methyl 2-hexenylacetoacetate.

EXAMPLE 2

Preparation of methyl 2-butylacetoacetate

The reaction mixture from the condensation of methyl acetoacetate (1.65 mol) and butyraldehyde (1.5 mol) with piperidine catalysis was hydrogenated in an autoclave at 50° C. with hydrogen and Pd/C catalysis. After the end of the hydrogenation and filtering off the Pd/C catalyst, the two-phase mixture was concentrated at a pressure of 15 mbar and a temperature of 70° C. The residue (246.33 g) still contained 2.16 percent of methyl 2-butenylacetoacetate and 5.0 percent of methyl acetoacetate. Sodium methoxide (5.32 g of a 5.4 molar solution) was added to this and this mixture was heated at 90° C. for about 4 hours. At the end of this treatment, 0.16 percent of methyl 2-butenylacetoacetate was still measured. The crude product was then distilled in a high-vacuum (3 to 4 mbar) in a thin-layer evaporator. The methyl 2-butylacetoacetate distillate (217.93 g), having a content of 94.4 percent, contained less than 0.1 percent of methyl 2-butenylacetoacetate. It was possible to obtain the produce in a yield of 72 percent based on butanol and with a purity of 99.8 percent. After a single fractionation process, the methyl 2-butenylacetoacetate content was less than 0.1 percent.

What is claimed is:

1. A process for the preparation of a pure alkyl alkylacetoacetates of the formula:

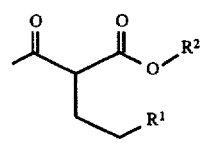

wherein $R^1$ is a $C_1$–$C_{10}$-alkyl group and $R^2$ is a $C_1$–$C_4$-alkyl group, from said alkyl alkylacetoacetate which contains an alkyl alkenylacetoacetate of the formula:

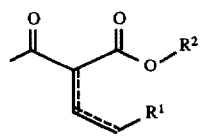

in which $R^1$ and $R^2$ have the above-stated meaning, and/or further by-products, converting the alkylalkenylacetoacetate acid ester of the formula II with an ester of the formula:

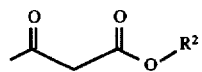

wherein $R^2$ has the above-stated meaning, in the presence of a strong base, into an intermediate which is separated off.

2. The process according to claim 1 wherein the strong base is an alkali metal alkoxide.

3. The process according to claim 2 wherein the ester of the formula III is methyl acetoacetate.

4. The process according to claim 3 wherein the reaction of the alkyl alkenylacetoacetate of formula II with the ester of the formula III is carried out at a temperature of from 50° to 150° C.

5. The process according to claim 1 wherein the ester of the formula III is methyl acetoacetate.

6. The process according to claim 1 wherein the reaction of the alkyl akenylacetoacetate of formula II with the ester of the formula III is carried out at a temperature of from 50° to 150° C.

* * * * *